US012394510B2

(12) United States Patent
Inaba et al.

(10) Patent No.: US 12,394,510 B2
(45) Date of Patent: Aug. 19, 2025

(54) FOOD PROVIDING SYSTEM, FOOD PROVIDING METHOD, AND PROGRAM

(71) Applicants: FANUC CORPORATION, Yamanashi (JP); NISSIN FOODS HOLDINGS CO., LTD., Osaka (JP)

(72) Inventors: Kiyonori Inaba, Yamanashi (JP); Masaru Oda, Yamanashi (JP); Kazuhisa Otsuka, Yamanashi (JP); Noritaka Ando, Osaka (JP); Yoichi Yoshida, Osaka (JP); Tetsuya Kawase, Osaka (JP)

(73) Assignees: FANUC CORPORATION, Yamanashi (JP); NISSIN FOODS HOLDINGS CO., LTD., Osaka (JP)

( * ) Notice: Subject to any disclaimer, the term of this patent is extended or adjusted under 35 U.S.C. 154(b) by 432 days.

(21) Appl. No.: 17/437,558

(22) PCT Filed: Nov. 26, 2019

(86) PCT No.: PCT/JP2019/046078
§ 371 (c)(1),
(2) Date: Sep. 9, 2021

(87) PCT Pub. No.: WO2020/194861
PCT Pub. Date: Oct. 1, 2020

(65) Prior Publication Data
US 2022/0148703 A1 May 12, 2022

(30) Foreign Application Priority Data
Mar. 25, 2019 (JP) .................................. 2019-056423

(51) Int. Cl.
*G16H 20/60* (2018.01)
*A47J 36/32* (2006.01)
(Continued)

(52) U.S. Cl.
CPC .............. *G16H 20/60* (2018.01); *A47J 36/32* (2013.01); *G06N 20/00* (2019.01); *G16H 50/30* (2018.01)

(58) Field of Classification Search
CPC ........ G06Q 10/08; G06Q 50/28; G06Q 50/12; G06Q 30/0601; G16H 20/60; G16H 50/30; G16H 40/20; A47J 36/32; G06N 20/00
See application file for complete search history.

(56) References Cited

U.S. PATENT DOCUMENTS 9,165,320 B1 * 10/2015 Belvin ............... G06Q 30/0633
9,824,152 B1 * 11/2017 Feller .................. G06F 16/9535
(Continued)

FOREIGN PATENT DOCUMENTS

CN     105718712     6/2016
CN     106372796     2/2017
(Continued)

OTHER PUBLICATIONS

International Search Report issued Jan. 21, 2020 in corresponding International Application No. PCT/JP2019/046078.
(Continued)

*Primary Examiner* — Florian M Zeender
*Assistant Examiner* — Vanessa Deligi
(74) *Attorney, Agent, or Firm* — Wenderoth, Lind & Ponack, L.L.P.

(57) ABSTRACT

The present invention makes a more appropriate suggestion concerning a meal of a user. A food providing system is provided with: an information acquisition unit for acquiring user information relating to a user as a food providing subject; a recipe suggestion unit for suggesting a plurality of recipes of dishes to the user on the basis of the user information; a recipe selection result acquisition unit for
(Continued)

acquiring a result of a selection by the user for the plurality of recipes suggested by the recipe suggestion unit; and a providing means selection result acquisition unit for acquiring a result of a selection by the user concerning providing means of food provided on the basis of the recipe.

12 Claims, 7 Drawing Sheets

(51) Int. Cl.
  *G06N 20/00* (2019.01)
  *G16H 50/30* (2018.01)

(56) References Cited

U.S. PATENT DOCUMENTS

| | | | | |
|---|---|---|---|---|
| 2003/0130908 A1* | 7/2003 | Hing | G06Q 30/0633 | 705/26.8 |
| 2004/0054592 A1* | 3/2004 | Hernblad | G06Q 20/322 | 705/15 |
| 2008/0077620 A1* | 3/2008 | Gilley | G16H 40/63 | |
| 2009/0075242 A1* | 3/2009 | Schwarzberg | G09B 19/0092 | 434/127 |
| 2009/0077007 A1* | 3/2009 | Schwarzberg | G06Q 30/02 | |
| 2009/0181131 A1* | 7/2009 | Forbes-Roberts | A23L 35/00 | 426/106 |
| 2010/0292998 A1* | 11/2010 | Bodlaender | G16H 20/60 | 705/2 |
| 2014/0089321 A1* | 3/2014 | Engel | G06Q 50/12 | 707/748 |
| 2015/0019354 A1* | 1/2015 | Chan | G06Q 10/109 | 99/325 |
| 2017/0046980 A1* | 2/2017 | Mehta | G09B 19/0092 | |
| 2018/0218461 A1* | 8/2018 | Pulley | G06Q 30/0643 | |
| 2019/0213914 A1* | 7/2019 | Vallance | G09B 19/0092 | |
| 2019/0228855 A1* | 7/2019 | Leifer | G06F 16/90324 | |
| 2019/0243922 A1* | 8/2019 | Pinel | G06F 16/24522 | |
| 2019/0370915 A1* | 12/2019 | Garden | G06N 20/00 | |
| 2020/0090060 A1* | 3/2020 | Murdoch | G06N 20/00 | |

FOREIGN PATENT DOCUMENTS

| | | |
|---|---|---|
| CN | 107833159 | 3/2018 |
| CN | 107977820 | 5/2018 |
| CN | 109036516 | 12/2018 |
| CN | 109255564 | 1/2019 |
| CN | 109256190 | 1/2019 |
| CN | 109300524 | 2/2019 |
| JP | 2004-5590 | 1/2004 |
| JP | 2005-56423 | 3/2005 |
| JP | 2005-157985 | 6/2005 |
| JP | 2006-350422 | 12/2006 |
| JP | 2014-93064 | 5/2014 |

OTHER PUBLICATIONS

Yajima, Asami, "Easy" cooking recipe recommendation considering user's conditions, 1st Forum on Data Engineering and Information Management—DEIM Forum—Proceedings, [online], May 2009, pp. 1-7, 4. System processing (with partial English translation).

* cited by examiner

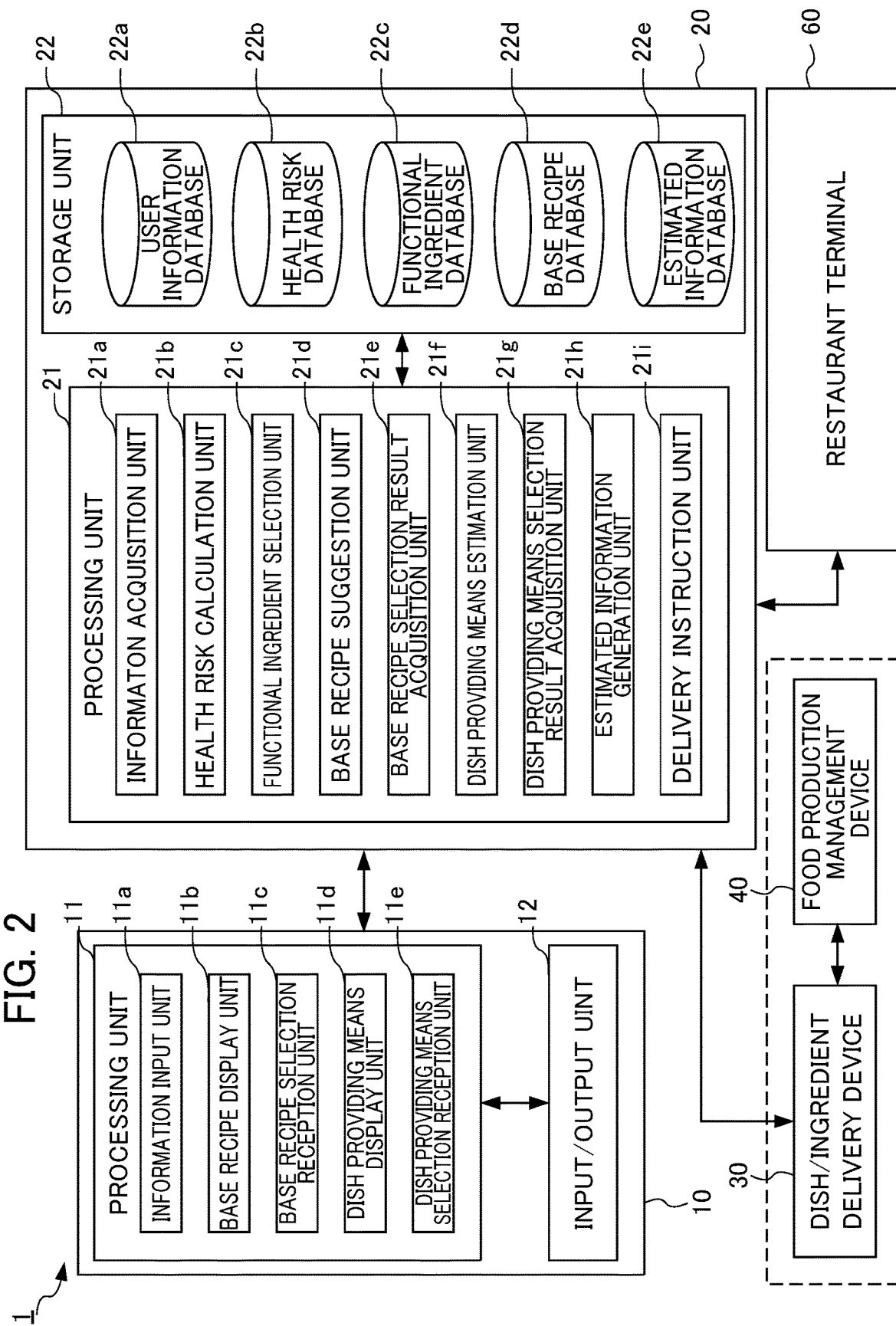

FIG. 3

| | NAME | AGE | SEX | HEIGHT[cm] | WEIGHT[kg] |
|---|---|---|---|---|---|
| BASIC INFORMATION | TARO SUZUKI | 42 | MALE | 175 | 70 |

| HEALTH RISK | | DIABETES MELLITUS | DYSLIPIDEMIA | OSTEOPOROSIS |
|---|---|---|---|---|
| GENE INFORMATION | DIABETES-RELATED GENES | 3 | | |
| | DYSLIPIDEMIA-RELATED GENES | | 1 | |
| | OSTEOPOROSIS-RELATED GENES | | | 1 |
| BIOLOGICAL INFORMATION | BLOOD PRESSURE | 1 | | |
| | BMI | 1 | 1 | |
| | BLOOD GLUCOSE LEVEL | 2 | | |
| | HbA1c | 1 | | |
| | HIGH LDL CHOLESTEROL | | 1 | |
| | LOW HDL CHOLESTEROL | | 1 | |
| | HIGH TRIGLYCERIDES | | 2 | |
| | BONE FORMATION MARKER LOW | | | |
| | BONE RESORPTION MARKER HIGH | | | |
| | LOW BONE DENSITY | | | 1 |
| LIFESTYLE INFORMATION | HIGH CALORIE | 1 | 2 | |
| | SMOKING | 1 | | 1 |
| | DRINKING ALCOHOL | | | |
| | DIABETES FAMILY HISTORY | 2 | | |
| | EXERCISE | | 1 | 1 |
| | CALCIUM INTAKE | | | 1 |
| | SUNLIGHT EXPOSURE TIME | | | |
| | | 12 | 9 | 4 |

| HEALTH RISK | TOTAL RISK INDEX | FUNCTIONAL INGREDIENT | | ADDITION |
|---|---|---|---|---|
| DIABETES MELLITUS | | 12 | COROSOLIC ACID | EVERY DAY |
| DYSLIPIDEMIA | | 9 | EPA・DHA | TIMES A WEEK |
| OSTEOPOROSIS | | 4 | SOYBEAN ISOFLAVONE | UNNECESSARY |

FIG. 4

| BASE RECIPE | HOME COOKING | | DELIVERY SERVICE | | RESTAURANT | |
|---|---|---|---|---|---|---|
| | ESTIMATED PRICE (YEN) | ESTIMATED REQUIRED TIME(H) | ESTIMATED PRICE (YEN) | ESTIMATED REQUIRED TIME(H) | ESTIMATED PRICE (YEN) | ESTIMATED REQUIRED TIME(H) |
| JAPANESE FOOD A | 400 | 0.4 | 800 | 0.9 | 1000 | 1.4 |
| JAPANESE FOOD B | 400 | 0.4 | 800 | 0.9 | 1000 | 1.4 |
| ITALIAN FOOD C | 1000 | 0.7 | 1800 | 1.2 | 2200 | 1.7 |
| ITALIAN FOOD D | 500 | 0.8 | 1000 | 1.3 | 1200 | 1.8 |
| CHINESE FOOD E | 800 | 0.5 | 1400 | 1.0 | 1800 | 1.5 |
| CHINESE FOOD F | 700 | 0.6 | 1200 | 1.1 | 1600 | 1.6 |
| : | : | : | : | : | : | : |

FIG. 7

YEAR/MONTH/DAY HOUR/MINUTE/SECOND

| | DISH PROVIDING MEANS | RECOMMENDED RECIPE | ESTIMATED REQUIRED TIME × ESTIMATED PRICE = COST INDEX | | |
|---|---|---|---|---|---|
| FATHER | RESTAURANT ▸ | JAPANESE FOOD A ▸ | 90 MINUTES | 2,160 YEN | 3,240 DECIDE |
| MOTHER | HOME COOKING ▸ | JAPANESE FOOD B ▸ | 30 MINUTES | 1,080 YEN | 540 DECIDE |
| SISTER | HOME COOKING ▸ | JAPANESE FOOD B ▸ | 30 MINUTES | 1,080 YEN | 540 DECIDE |
| BROTHER | DELIVERY SERVICE ▸ | ITALIAN FOOD C ▸ | 60 MINUTES | 1,560 YEN | 1,560 DECIDE |
| | | | SUBTOTAL | 5,880 YEN | 5,880 |

FOOD PROVIDING SYSTEM, FOOD PROVIDING METHOD, AND PROGRAM

TECHNICAL FIELD

The present invention relates to a food providing system, a food providing method, and a program.

BACKGROUND ART

In recent years, there has been a growing need to reduce the labor and time required for cooking as much as possible due to the increase in dual-income households or other reasons. In response to this need, there is a concern that using restaurants or delivery services may result in unbalanced nutrition and higher unit prices per meal, although it saves the labor and time of cooking. Here, various technologies have been suggested to assist users in eating by using information processing technology. For example, Japanese Unexamined Patent Application, Publication No. 2005-157985 discloses an ingredient providing system that provides the user with menus and ingredients suitable for health management based on the vital information of the user.
Patent Document 1: Japanese Unexamined Patent Application, Publication No. 2005-157985

DISCLOSURE OF THE INVENTION

Problems to be Solved by the Invention

However, when a meal menu or the like is suggested to the user, it is desired to make the suggestion more appropriate for the user taking into account various aspects such as the preferences, schedule, and family composition of the user.

It is an object of the present invention to make a more appropriate suggestion for a meal for a user.

Means for Solving the Problems (1) An aspect of the present disclosure relates to a food providing system including an information acquisition unit that acquires user information on a user to whom food is to be provided, a recipe suggestion unit that suggests a plurality of recipes for dishes to the user based on the user information, a recipe selection result acquisition unit that acquires a result of a selection by the user from the plurality of recipes suggested by the recipe suggestion unit, and a providing means selection result acquisition unit that acquires a result of a selection by the user for a providing means for a food provided based on the recipe.

(2) An aspect of the present disclosure relates to a food providing method executed by a food providing system that provides a food to a user. The food providing method includes an information acquisition step of acquiring user information on the user to whom food is to be provided, a recipe suggestion step of suggesting a plurality of recipes for dishes to the user based on the user information, a recipe selection result acquisition step of acquiring a result of a selection by the user from the plurality of recipes suggested in the recipe suggestion step, and a providing means selection result acquisition step of acquiring a result of a selection by the user for a providing means for a food provided based on the recipe.

(3) An aspect of the present disclosure relates to a program, causing a computer to realize an information acquisition function of acquiring user information on a user to whom food is to be provided, a recipe suggestion function of suggesting a plurality of recipes for dishes to the user based on the user information, a recipe selection result acquisition function of acquiring a result of a selection by the user from the plurality of recipes suggested by the recipe suggestion function, and a providing means selection result acquisition function of acquiring a result of a selection by the user for a providing means for a food provided based on the recipe.

Effects of the Invention

According to one aspect, it is possible to make a more appropriate suggestion for a meal for a user.

BRIEF DESCRIPTION OF THE DRAWINGS

FIG. 2 is a block diagram showing the functional configuration of the food providing system;

FIG. 3 is a schematic diagram showing an example of health risk data stored in a health risk database;

FIG. 4 is a schematic diagram showing an example of a required time and price estimation table in which required times and estimated prices are defined;

FIG. 7 is a schematic diagram showing an example of a suggestion screen provided from a system management server to a terminal device.

PREFERRED MODE FOR CARRYING OUT THE INVENTION

Figure 1:
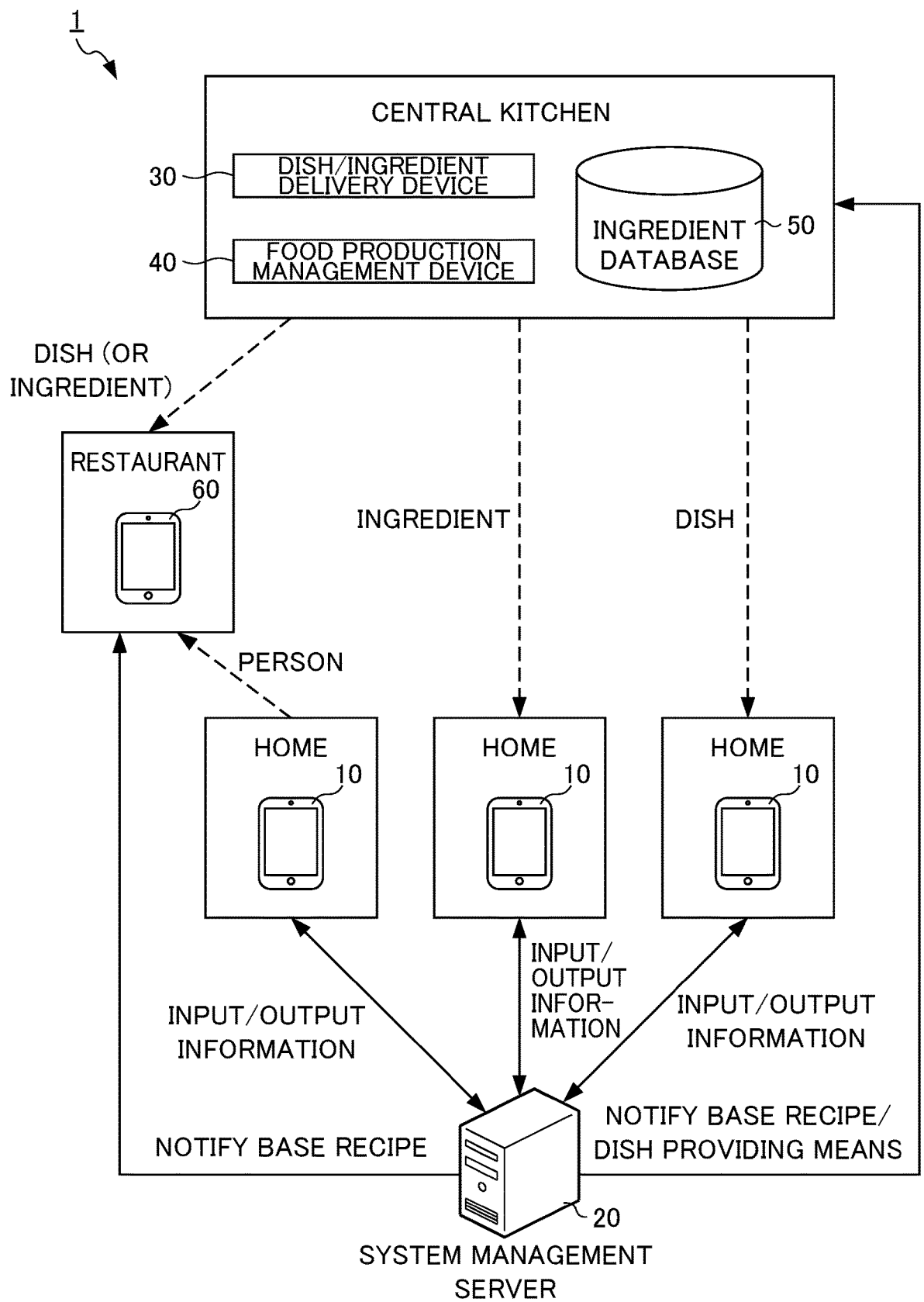
FIG. 1 is a schematic diagram showing an example of a system form of a food providing system.

Embodiments of the present invention will be described below with reference to the drawings.
[Configuration]
FIG. 1 is a schematic diagram showing an example of a system form of a food providing system 1. As shown in FIG. 1, the food providing system 1 is installed in a home of a user (here, an eater), a central kitchen, and a restaurant. The food providing system 1 includes a terminal device 10 installed in the user's home, a system management server 20 that manages the entire system, a dish/ingredient delivery device 30 as a cooking instruction unit installed in the central kitchen, a food production management device 40, an ingredient database 50, and a restaurant terminal 60 installed in the restaurant. The respective devices included in the food providing system 1 are connected to one another via a network such as the Internet. In FIG. 1, a solid line represents transmission and reception of information, and a dotted line represents the movement of a person or a food (dish or ingredient). In the present embodiment, the central kitchen is a facility for producing a dish or delivering ingredients in accordance with a selection by the user, and the restaurant is a facility for providing meals. In the following description, a recipe on which a dish or ingredients provided by the food providing system 1 is based is referred to as a "base recipe" as appropriate.

In FIG. 1, by transmitting and receiving input/output information (e.g., the information on the user, suggested base recipe, results of selection of a base recipe and a dish providing means by the user described later) between the terminal device 10 installed in the user's home and the system management server 20, a dish or ingredients of a recipe desired by the user and its providing means (either home cooking in which ingredients are delivered to the home, a delivery service to deliver a dish to the home, or a restaurant to deliver a dish (or ingredients) to the restaurant and serve the dish at the restaurant) are determined. Note that the restaurant of the present embodiment is provided together with the central kitchen, and when the user selects that a dish be served at the restaurant, the dish produced in the central kitchen is delivered to the restaurant. In this regard, however, the ingredients of the base recipe may be delivered to the restaurant and cooked, and the dish then served at the restaurant.

The system management server 20 notifies the results of selections (base recipe and dish providing means) by the user to the dish/ingredient delivery device 30 installed in the central kitchen. The dish/ingredient delivery device 30 refers to an ingredient database 50 in which the inventory data of ingredients is stored and in accordance with the results of selections by the user notified from the system management server 20 and arranges for the preparation of the dish or ingredients. Specifically, when the user selects delivery of a dish to the home or the restaurant as providing means, the dish/ingredient delivery device 30 requests the food production management device 40 to produce the dish based on the base recipe. When the user selects delivery of ingredients to the home as providing means, the dish/ingredient delivery device 30 causes ingredients based on the base recipe to be taken from inventory. The dish/ingredient delivery device 30 arranges for delivering a prepared dish or prepared ingredients to a predetermined delivery destination (home or restaurant). Note that it is possible to take ingredients from inventory and deliver a dish or ingredients manually or automatically.

In response to a request from the dish/ingredient delivery device 30, the food production management device 40 produces the dish of a base recipe selected by the user. The food production management device 40 may include, for example, a cooker, a robot, or the like, and may produce the dish based on the base recipe. The ingredient database 50 stores information on the inventory of ingredients prepared in the central kitchen. The restaurant terminal 60 displays information (such as a base recipe selected by the user) notified from the system management server 20.

FIG. 2 is a block diagram showing the functional configuration of the food providing system 1. FIG. 2 mainly shows the functional configuration realized by executing a program by the terminal device 10 and the system management server 20. Each device shown in FIG. 2 may be configured by, for example, an information processing device such as a personal computer (PC) or a server computer (for each terminal, a portable terminal including a tablet terminal, a smart phone, a wearable terminal, or the like), and each of these devices includes a processing unit including a central processing unit (CPU) or the like, a storage unit including a hard disk, a semiconductor memory, or the like, and an input/output unit including a keyboard, a display (or a touch panel), or the like. Each of these devices includes various hardware constituting an information processing device, such as a memory (not shown) and a communication device, in addition to the processing unit, the storage unit, and the input/output unit.

As shown in FIG. 2, the terminal device 10 includes a processing unit 11 and an input/output unit 12, and as the functional configuration, the processing unit 11 includes an information input unit 11a, a base recipe display unit 11b, a base recipe selection reception unit 11c, a dish providing means display unit 11d, and a dish providing means selection reception unit 11e. The information input unit 11a receives input of various types of information by the user, such as information on the user, a result of a selection of a suggested base recipe, and a result of a selection of a suggested food providing means on a user interface screen (UI screen).

In the present embodiment, examples of the information on the user input via the information input unit 11a include the following.

Age, sex, and medical history of the user
Schedule for the user
Household status of the user
Social event
Fatigue of the user
Weather/temperature/atmospheric pressure
History of recent base recipe selections
Allergy information of the user
Gene information, biological information and lifestyle information of the user
Schedule for a cook and schedule for a family member
Family composition (family type, etc.)
Fatigue of a cook Among these, regarding the fatigue of the user and a cook and weather/temperature/atmospheric pressure, values measured (measured values) in real time by various sensors may be input. Regarding the other information on the user, values (prior information) input in advance may be used. Regarding information that is not limited to the user, such as a social event, and weather/temperature/atmospheric pressure, the system management server 20 may acquire information from an external server or the like as appropriate.

The base recipe display unit 11b displays base recipes (suggested base recipe candidates) transmitted from the system management server 20 on the UI screen. The base recipe selection reception unit 11c receives a selection by the user for the suggested base recipes on the UI screen. The dish providing means display unit 11d displays dish providing means (suggested dish providing means candidates) transmitted from the system management server 20 on the UI screen. The dish providing means selection reception unit 11e receives a selection by the user for the suggested dish providing means on the UI screen.

As described above, in the present embodiment, the user can select "home cooking", "delivery service", and "restaurant" as dish providing means, and in each case, the "estimated price" and "estimated required time" for providing the dish are presented from the system management server 20 (see FIG. 7). When "home cooking" is selected as dish providing means, the user performs cooking by himself/herself (or a family cook) based on a presented base recipe. For ingredients, ingredients stored in the refrigerator at home are used in principle, and for ingredients that are insufficient, delivery of the ingredients can be requested to the system management server 20 manually or automatically using inventory information in a refrigerator having an inventory management function, for example, through the terminal device 10. In this case, the estimated price is calculated based on the ingredients required for the base recipe and the market price of the ingredients, but it may be calculated based on the user's purchase history. The estimated required time is calculated based on the average time required for a housewife to cook the base recipe, but may be calculated based on a history of the user's past cooking times, the degree of fatigue of the cook, or the like.

When "delivery service" is selected as dish providing means, a cooked dish based on a selected base recipe is delivered to the home. At this time, the estimated price is calculated based on a preset price of the dish, but the price may be varied according to the degree of order congestion. The estimated required time can be a total value of the time required for cooking and the time required for delivery.

When "restaurant" is selected as dish providing means, a cooked dish based on a selected base recipe is delivered to the restaurant and served to the user. It is also possible to allow the user to select a desired restaurant from a plurality of restaurants. In the present embodiment, as reference information for the user to select a base recipe and dish providing means, in addition to "estimated price" and "estimated required time", "cost index" calculated as "estimated price×estimated required time" is presented (see FIG. 7).

The system management server 20 includes a processing unit 21 and a storage unit 22. Further, in the system management server 20, as the functional configuration, the processing unit 21 includes an information acquisition unit 21a, a health risk calculation unit 21b, a functional ingredient selection unit 21c, a base recipe suggestion unit 21d as a recipe suggestion unit, a base recipe selection result acquisition unit 21e as a recipe selection result acquisition unit, a dish providing means estimation unit 21f as a providing means estimation unit, a dish providing means selection result acquisition unit 21g as a providing means selection result acquisition unit, an estimated information generation unit 21h, and a delivery instruction unit 21i as a food delivery instruction unit. The storage unit 22 includes a user information database 22a, a health risk database 22b, a functional ingredient database 22c, a base recipe database 22d, and an estimated information database 22e.

The user information database 22a stores information on the attributes of the user, such as the user's name, age, sex, family composition, schedule, medical history, allergy information, and preference, and various information on the user, such as the user's selection histories of base recipes and dish providing means. The health risk database 22b stores information indicating the relationship between a health risk factor and a health risk (hereinafter referred to as "health risk data").

FIG. 3 is a schematic diagram showing an example of health risk data stored in the health risk database 22b. As shown in FIG. 3, the health risk data is defined for each user, and gene information, biological information, and lifestyle information are listed as health risk factors, and health risks (relevant disease names) with respect to these health risk factors are shown in association with each other. In the example shown in FIG. 3, the correspondence relationship between a health risk factor and a health risk (relevant disease names) is indicated by a risk index (1 to 3) indicating the degree of relevance.

The functional ingredient database 22c stores data in the form of a table in which a health risk factor and a functional ingredient effective for the health risk factor are associated with each other. In the base recipe database 22d, the names of a plurality of base recipes and the contents of the base recipes (ingredients and cooking methods) are stored in association with each other. The estimated information database 22e stores data in the form of a table (hereinafter referred to as a "required time/price estimation table") in which the estimated required time and the estimated price are defined for each base recipe when provided by each dish providing means.

FIG. 4 is a schematic diagram showing an example of a required time and price estimation table in which required times and estimated prices are defined. As shown in FIG. 4, in the required time/price estimation table, estimated required times and estimated prices when "home cooking", "delivery", or "restaurant" is selected for each selectable base recipe are defined in advance. As the estimated price, a preset price of the dish is defined, but the estimated price may be varied in accordance with individual situations such as the congestion of a restaurant. Further, as the estimated required time, a total of the time required for cooking and additional required times such as a waiting time before entering a restaurant may be defined.

The information acquisition unit 21a acquires information on the user input to the terminal device 10. The information acquisition unit 21a stores the acquired information in the user information database 22a in association with information for identifying the user. The health risk calculation unit 21b refers to the user information database 22a and the health risk database 22b, and calculates a risk index for a health risk (relevant disease name) of the user based on health risk factors of the user. For example, the health risk calculation unit 21b refers to the user information database 22a and the health risk database 22b, totals the risk indices of the health risk factors associated with a specific health risk (disease) of the user, and calculates the risk index of the user.

The functional ingredient selection unit 21c refers to the user information database 22a and the functional ingredient database 22c, and selects a functional ingredient that is effective for a health risk for which the total of the risk indices is equal to or greater than the first threshold value (e.g., 5). For example, the functional ingredient selection unit 21c refers to the data in the form of a table of the functional ingredient database 22c, and selects a functional ingredient associated with a specified health risk. In general, it is known that corosolic acid is effective for diabetes mellitus, EPA and DHA are effective for dyslipidemia, and soybean isoflavone is effective for osteoporosis. For example, in the example shown in FIG. 3, for the health risks of diabetes mellitus and dyslipidemia, in which the total of the risk indices is equal to or greater than the first threshold value (5 here), the corresponding functional ingredients, namely, corosolic acid, and EPA and DHA, are respectively selected. The amount and the frequency of addition of the functional ingredient can be determined according to the total value of risk indices. When a functional ingredient is selected, the selected functional ingredient is added to a base recipe selected by the user, and then a dish or ingredients based on the recipe are provided.

The base recipe suggestion unit 21d refers to the user information database 22a, and suggests a base recipe suitable for a user as a suggestion target for the base recipe by using a machine learning model constructed by machine learning (hereinafter referred to as a "base recipe suggestion model") based on the information on the user. In the present embodiment, the base recipe suggestion model of the base recipe suggestion unit 21d may calculate the selection probability of each base recipe by totaling the number of base recipes selected in the past by a plurality of users having the same feature quantities for each base recipe and dividing it by the total value in information on users. That is, the base recipe suggestion unit 21d can output base recipes (present expected base recipes in descending order of probability) with respect to input information of the user in terms of probability, based on past statistics of a plurality of users. The base recipe suggestion model used at this time is constructed by a machine learning unit 100 included in the base recipe suggestion unit 21d.

Figure 5:
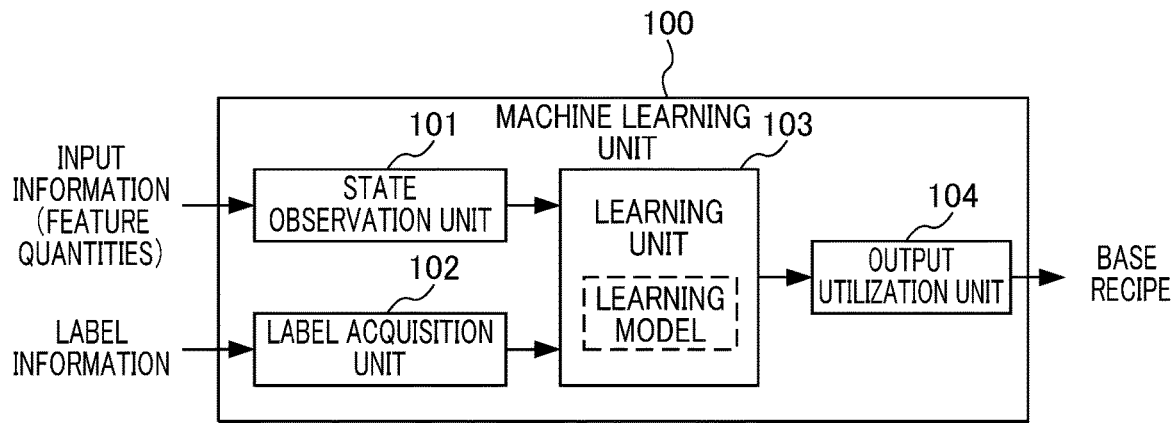
FIG. 5 is a block diagram showing the functional configuration of a machine learning unit in a base recipe suggestion unit.

FIG. 5 is a block diagram showing the functional configuration of the machine learning unit 100 in the base recipe suggestion unit 21d. As shown in FIG. 5, the machine learning unit 100 includes a state observation unit 101, a label acquisition unit 102, a learning unit 103, and an output utilization unit 104. The state observation unit 101 acquires input information (feature quantities) used in machine learning. For example, the state observation unit 101 acquires "user's age, sex, and medical history", "user's schedule", "social event", "user's fatigue", "weather, temperature, and atmospheric pressure", "history of recent base recipe selections", "user's allergy information", and the like as input information (feature quantities).

The label acquisition unit 102 acquires label information used as teaching data in machine learning. For example, the label acquisition unit 102 acquires information on base recipes (herein, the names of the base recipes) selected by users having the same input information (feature quantities) in the past. At this time, the information on base recipes can be selected for a base recipe having the highest selected frequency or a predetermined number of base recipes having higher selected frequencies. As the information on base recipes, the selection probability of each base recipe for users having the same input information (feature quantities) may be used, as described above. Thus, it is possible to learn a learning model that outputs the selection probability of each base recipe for users having the same input information (feature quantities). The learning unit 103 constructs a base recipe suggestion model (machine learning model) by performing supervised learning using input information (feature quantities) acquired by the state observation unit 101 and label information (information on base recipes) acquired by the label acquisition unit 102 as input. Alternatively, the learning unit 103 may construct a base recipe suggestion model (machine learning model) by performing supervised or unsupervised machine learning using classification or clustering.

When information for suggesting a base recipe is input, the output utilization unit 104 performs inference using a base recipe suggestion model, and outputs a base recipe suitable for the user. For example, a base recipe with the highest selection probability may be output. Since "history of recent base recipe selections" is acquired as input information, the output utilization unit 104 can also make suggestions while avoiding base recipes that overlap with suggestions made within a predetermined period in the past.

The base recipe selection result acquisition unit 21e acquires information on a base recipe selected by the user from base recipe candidates suggested by the base recipe suggestion unit 21d. The dish providing means estimation unit 21f refers to the user information database 22a, and estimates a dish providing means suitable for a user as an estimation target for the dish providing means by using a machine learning model constructed by machine learning (hereinafter referred to as a "dish providing means estimation model") based on information on the user. In the present embodiment, the dish providing means estimation model of the dish providing means estimation unit 21f may calculate the selection probability of each dish providing means by totalizing the number of dish providing means selected in the past by a plurality of users having the same feature quantities for each dish providing means and dividing it by the total value in information on users. That is, the base recipe selection result acquisition unit 21e outputs dish providing means (presents expected dish providing means in descending order of probability) with respect to input information of the user in terms of probability, based on past statistics of a plurality of users. The dish providing means estimation model used at this time is constructed by the machine learning unit 200 included in the dish providing means estimation unit 21f.

Figure 6:
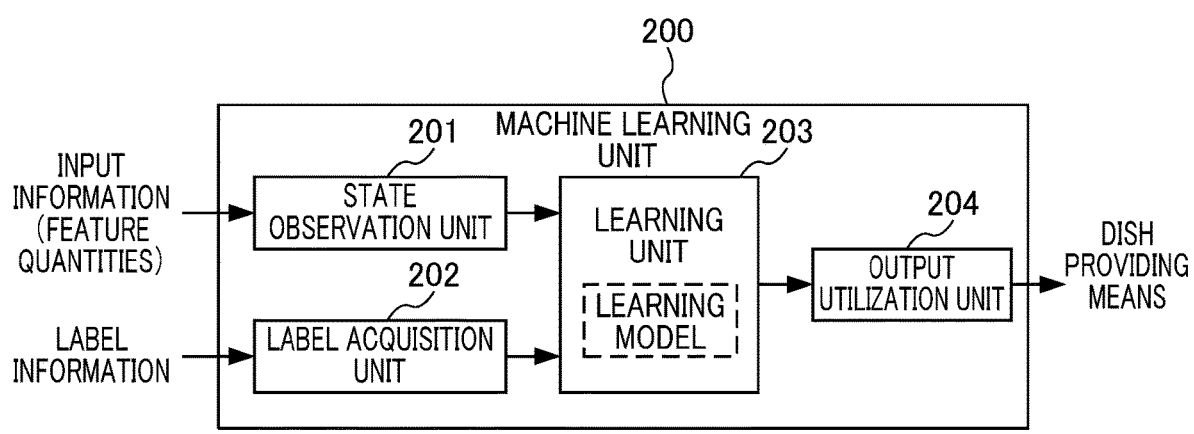
FIG. 6 is a block diagram showing the functional configuration of a machine learning unit in a dish providing means estimation unit.

FIG. 6 is a block diagram showing the functional configuration of the machine learning unit 200 in the dish providing means estimation unit 21f. As shown in FIG. 6, the machine learning unit 200 includes a state observation unit 201, a label acquisition unit 202, a learning unit 203, and an output utilization unit 204. The state observation unit 201 acquires input information (feature quantities) used in machine learning. For example, the state observation unit 201 acquires "user's age, sex, and medical history", "schedule for a cook and schedule for a family member" "family composition", "fatigue of a cook", "social event", "weather, temperature, and atmospheric pressure", and the like as input information (feature quantities).

The label acquisition unit 202 acquires label information used as teaching data in machine learning. For example, the label acquisition unit 202 acquires information on dish providing means selected by users having the same input information (feature quantities) in the past (here, the specific content of the dish providing means). At this time, the information on dish providing means can be selected for a dish providing means having the highest selected frequency or a predetermined number of dish providing means having higher selected frequencies. As the information on dish providing means, the selection probability of each dish providing means for users having the same input information (feature quantities) may be used, as described above. Thus, it is possible to learn a learning model that outputs the selection probability of each dish providing means for users having the same input information (feature quantities). The learning unit 203 constructs a dish providing means estimation model (machine learning model) by performing supervised learning using input information (feature quantities) acquired by the state observation unit 201 and label information (information on dish providing means) acquired by the label acquisition unit 202 as input. Alternatively, the learning unit 203 may construct a dish providing means estimation model (machine learning model) by performing supervised or unsupervised machine learning using classification or clustering. When information for suggesting dish providing means is input, the output utilization unit 204 performs inference using a dish providing means estimation model, and outputs dish providing means suitable for the user. For example, dish providing means having the highest selection probability may be output.

The dish providing means selection result acquisition unit 21g acquires information on dish providing means selected by the user from dish providing means candidates suggested by the dish providing means estimation unit 21f. The estimated information generation unit 21h calculates an estimated price and an estimated required time when a base recipe and dish providing means are selected based on suggested base recipes and dish providing means. In the present embodiment, the estimated information generation unit 21h also calculates a cost index calculated as an estimated price×an estimated required time.

When results selected by the user from suggested base recipes and dish providing means are acquired, the delivery instruction unit 21i transmits a base recipe and dish providing means based on the results selected by the user to the dish/ingredient delivery device 30. When a functional ingredient is selected by the functional ingredient selection unit 21c, the delivery instruction unit 21i adds the selected functional ingredient to the base recipe and transmits the base recipe. As a result, a delivery instruction to the dish/ingredient delivery device 30 is completed. Various information output from the system management server 20 is transmitted to the terminal device 10, and displayed as a UI screen for displaying the contents of suggestions (hereinafter referred to as a "suggestion screen").

FIG. 7 is a schematic diagram showing an example of a suggestion screen provided from the system management server 20 to the terminal device 10. As shown in FIG. 7, the suggestion screen provided from the system management server 20 to the terminal device 10 displays dish providing means candidates, base recipe candidates (recommended recipes), estimated required times, estimated prices, and cost indices for the user and the user's family members. A dish providing means candidate and a base recipe candidate with the highest selection probability in the past are displayed among suggested candidates, and the other candidates can be selected by pull-down menus. As for the estimated required time and the estimated price, times and prices calculated by the system management server 20 are displayed, and cost indices calculated from the estimated required times and the estimated prices are displayed.

On the suggestion screen shown in FIG. 7, dishes or ingredients to be provided to the user and each family member and providing means thereof are fixed by selecting the contents desired by the user and each family member from the pull-down menus and operating the "Decide" button for fixing the selection results. Then, the fixed selection results are transmitted from the terminal device 10 to the system management server 20. When a specific base recipe is selected on the suggestion screen, only a limited dish providing means may be selectable. For example, for dishes requiring special cooking appliances or equipment, only restaurants can be selected as the dish providing means.

[Operation]

Figure 8:
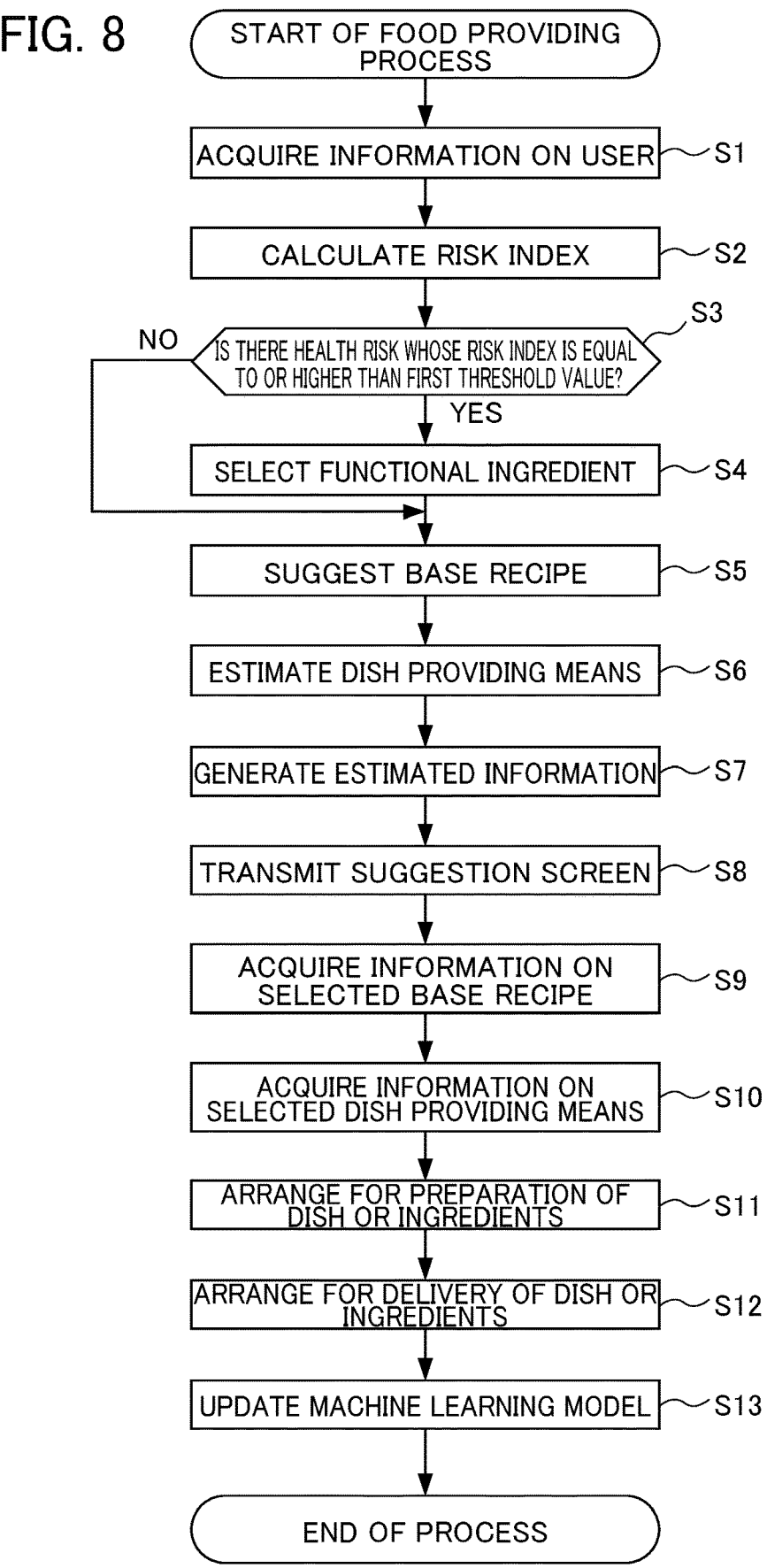
FIG. 8 is a flowchart illustrating a flow of a food providing process executed by the food providing system.

Next, the operation of the food providing system 1 will be described. FIG. 8 is a flowchart illustrating a flow of a food providing process executed by the food providing system 1. The food providing process is a process executed by the terminal device 10, the system management server 20, the dish/ingredient delivery device 30, the food production management device 40, the ingredient database 50, and the restaurant terminal 60 in cooperation. The food providing process commences when an operation of starting the food providing process is input in the terminal device 10.

When the food providing process commences, in Step S1, the information acquisition unit 21a in the system management server 20 acquires information on the user input on the UI screen of the terminal device 10. At this time, the acquired information is stored in the user information database 22a in association with information for identifying the user. In Step S2, the health risk calculation unit 21b refers to the user information database 22a and the health risk database 22b, and calculates a risk index for a health risk (relevant disease name) of the user based on health risk factors of the user.

In Step S3, the functional ingredient selection unit 21c determines whether there is a health risk whose risk index is equal to or higher than the first threshold value (5 in this case). If there is no health risk whose risk index is equal to or higher than the first threshold value, NO is determined in Step S3, and the process proceeds to Step S5. If there is a health risk whose risk index is equal to or higher than the first threshold value, YES is determined in Step S3, and the process proceeds to Step S4.

In Step S4, the functional ingredient selection unit 21c refers to the data in the form of a table of the functional ingredient database 22c, and selects a functional ingredient associated with a health risk whose risk index is equal to or greater than the first threshold value. In Step S5, the base recipe suggestion unit 21d refers to the user information database 22a, and suggests a base recipe suitable for a user as a suggestion target for the base recipe by using a base recipe suggestion model (machine learning model) constructed by machine learning on the basis of the information on the user.

In Step S6, the dish providing means estimation unit 21f refers to the user information database 22a, and estimates a dish providing means suitable for a user as an estimation target for the dish providing means by using a dish providing means estimation model (machine learning model) constructed by machine learning on the basis of the information on the user. In Step S7, the estimated information generation unit 21h calculates an estimated price and an estimated required time when a base recipe and dish providing means are selected by the user based on suggested base recipes and dish providing means (generates estimated information). In Step S8, the estimated information generation unit 21h transmits to the terminal device 10 the data of the suggestion screen formed by adding the estimated information.

In Step S9, the base recipe selection result acquisition unit 21e acquires information on a base recipe selected by the user from base recipe candidates displayed on the suggestion screen. In Step S10, the dish providing means selection result acquisition unit 21g acquires information on a dish providing means selected by the user from dish providing means candidates displayed on the suggestion screen. The information on the base recipe and the dish providing means that are selected by the user is transmitted to the dish/ingredient delivery device 30 by the delivery instruction unit 21i. When a functional ingredient is selected by the functional ingredient selection unit 21c, the selected functional ingredient is added to the base recipe and transmitted.

In Step S11, the dish/ingredient delivery device 30 refers to the ingredient database 50 in which the inventory data of ingredients is stored in accordance with the selection results of the user notified from the system management server 20. Specifically, when the user selects delivery of a dish to the home or a restaurant, the dish/ingredient delivery device 30 requests the food production management device 40 to produce the dish of the base recipe selected by the user. In response to this, the food production management device 40 produces the dish of the base recipe requested. Further, when the dish providing means selected by the user is delivery of ingredients, the dish/ingredient delivery device 30 takes ingredients based on the base recipe from inventory.

In Step S12, the dish/ingredient delivery device 30 arranges for delivering a prepared dish or ingredients to a predetermined delivery destination (home or restaurant). At this time, the terminal device 10 and the restaurant terminal 60 are notified that the dish or ingredients will be delivered. As a result, the result of the suggestion of the dish or ingredients in the food providing system 1 is determined. In Step S13, the machine learning unit 100 of the base recipe suggestion unit 21d and the machine learning unit 200 of the dish providing means estimation unit 21f update the machine learning models. Specifically, the machine learning unit 100 of the base recipe suggestion unit 21d updates the base recipe suggestion model (machine learning model) by performing supervised learning using input information (feature quantities) and label information (information on the base recipe) as input. The machine learning unit 200 of the dish providing means estimation unit 21*f* updates the dish providing means estimation model (machine learning model) by performing supervised learning using input information (feature quantities) and label information (information on the dish providing means) as input. The update of the machine learning models may be performed collectively at a predetermined time (e.g., 3:00 a.m.). After Step S13, the food providing process ends.

By such a process, the food providing system 1 suggests a base recipe suitable for a user as a suggestion target for the base recipe by using a base recipe suggestion model constructed by machine learning based on information on the user. Further, the food providing system 1 suggests dish providing means suitable for a user as an estimation target for the dish providing means by using a dish providing means estimation model constructed by machine learning based on information on the user. In the food providing system 1, various viewpoints such as user's age and sex, a schedule, a social event, fatigue, weather, temperature, and atmospheric pressure are taken into consideration as information on the user. Such suggested base recipes and dish providing means each have a high selection probability from having been selected in the past by a plurality of users having the same feature quantities as the information on the user. Then, when the user selects a desired one from each of suggested base recipes and dish providing means, a dish or ingredients based on the selected base recipe is provided to the user by the selected dish providing means. Therefore, according to the food providing system 1, it is possible to make a more appropriate suggestion regarding a meal for a user.

[Modification 1]

In the above-described embodiment, the food providing system 1 can realize a function for more efficiently performing delivery to a home or a restaurant. That is, the dish/ingredient delivery device 30 can group orders (selections of base recipes and dish providing means by users) whose scheduled eating time is within a predetermined period of time, and classify orders corresponding to the same base recipe among orders in the same group as a subgroup. Based on this classification, a plurality of schedules for ordered cooking are adjusted, and orders whose scheduled eating time is within a predetermined period of time (e.g., within 15 minutes) can be collectively delivered. The dish/ingredient delivery device 30 can also plan personnel or the placement of a vehicle assigned to delivery of a dish or ingredients based on the selection probability of each suggested dish providing means. These functions enable the food providing system 1 to provide dishes or ingredients more efficiently.

<Effects of the Present Embodiments>

Embodiments of the present disclosure are listed below.

(1) According to the present embodiment, a food providing system 1 includes an information acquisition unit 21*a* that acquires user information on a user to whom food is to be provided, a base recipe suggestion unit 21*d* that suggests a plurality of recipes for dishes to the user based on the user information, a base recipe selection result acquisition unit 21*e* that acquires a result of a selection by the user from the plurality of recipes suggested by the base recipe suggestion unit 21*d*, and a dish providing means selection result acquisition unit 21*g* that acquires a result of a selection by the user for a dish providing means of the dish provided based on the recipe. This makes it possible to make a more appropriate suggestion regarding a meal for the user.

(2) The food providing system 1 described in (1) may include a functional ingredient selection unit 21*c* that selects a functional ingredient effective for a health risk based on the user information. This makes it possible to provide a dish that reduces a health risk of the user.

(3) In the food providing system 1 of (1) or (2), the base recipe suggestion unit 21*d* may include a state observation unit 101 that acquires data relating to at least one of age/sex/medical history/allergy information of the user, a schedule for the user, fatigue of the user, gene information of the user, biological information and lifestyle information of the user, weather/temperature/atmospheric pressure, a social event, and a history of recent recipe selections, as input data, a label acquisition unit 102 that acquires a recipe selected in a past as a label, and a learning unit 103 that constructs a learning model for suggesting a recipe by performing supervised learning using a pair of input data acquired by the state observation unit 101 and the label acquired by the label acquisition unit 102 as teaching data. This makes it possible to infer output (base recipe) for input information of the user, based on the past statistics of a plurality of users.

(4) The food providing system 1 of (2) may further include a health risk calculation unit 21*b* that calculates a risk index for the health risk of the user based on the user information. The functional ingredient selection unit 21*c* may select the functional ingredient effective for the health risk based on the risk index calculated by the health risk calculation unit 21*b*. This makes it possible to select a functional ingredient according to the degree of a risk in the health of the user.

(5) In the food providing system 1 according to (1) to (4), the dish providing means may include at least delivery of an ingredient to a home, delivery of a cooked dish to the home, and serving of a dish at a restaurant. This makes it possible to provide a food to the user in various forms.

(6) The food providing system 1 according to (1) to (5) may further include a dish providing means estimation unit 21*f* that estimates a selection probability of the dish providing means based on the user information. This makes it possible to suggest a dish providing means that is highly likely to be selected by the user.

(7) In the food providing system 1 of (6), the dish providing means estimation unit 21*f* may include a state observation unit 201 that acquires data relating to at least one of a schedule for the user, schedule for a family member of the user, schedule for a cook, a social event, family composition, fatigue of the user, weather/temperature/atmospheric pressure, a history of recent dish providing means selections, and a household status, as input data; a label acquisition unit 202 that acquires selected dish providing means as a label; and a learning unit 203 that constructs a learning model for estimating a selection probability of each dish providing means from a plurality of dish providing means suggested to the user by performing supervised learning using a pair of the input data acquired by the state observation unit 201 and the label acquired by the label acquisition unit 202 as teaching data. This makes it possible to infer output (dish providing means) for input information of the user, based on the past statistics of a plurality of users.

(8) The food providing system 1 according to (1) to (7) may include a delivery instruction unit 21*i* that instructs delivery of an ingredient necessary for the recipe and a functional ingredient effective for a health risk, if any, to a home or a facility for producing a dish based on the dish providing means selected by the user. This makes it possible to promptly deliver an ingredient necessary for a recipe and a functional ingredient effective for a health risk to an appropriate delivery destination.

(9) The food providing system 1 of (8) may include a food production management device 40 that cooks a dish ordered by the user, and a dish/ingredient delivery device 30 that instructs the food production management device 40 to cook the dish corresponding to the recipe and with the functional ingredient added. The delivery instruction unit 21*i* may instruct delivery of the dish cooked by the food production management device 40 to the home or a restaurant based on the dish providing means selected by the user. Thereby, when the user selects delivery of a dish, the dish can be promptly produced from an ingredient based on a recipe and delivered to a predetermined delivery destination.

(10) In the food providing system 1 of (9), the dish/ingredient delivery device 30 may group orders whose scheduled eating time is within a predetermined period of time, classify orders corresponding to a same recipe among orders in a same group as a subgroup, and adjust a plurality of schedules for ordered cooking based on the classification. This enables the food providing system 1 to more efficiently provide dishes or ingredients.

(11) In the food providing system 1 of (9) or (10), the delivery instruction unit 21*i* may plan personnel or a vehicle to be allocated to delivery based on a selection probability of each of the dish providing means estimated based on the user information. This enables the food providing system 1 to more efficiently provide dishes or ingredients.

(12) According to the present embodiment, a food providing method executed by a food providing system 1 that provides a food to a user includes an information acquisition step of acquiring user information on the user to whom food is to be provided, a recipe suggestion step of suggesting a plurality of recipes for dishes to the user based on the user information, a recipe selection result acquisition step of acquiring a result of a selection by the user from the plurality of recipes suggested in the recipe suggestion step, and a providing means selection result acquisition step of acquiring a result of a selection by the user for a dish providing means for the dish provided based on the recipe. This makes it possible to make a more appropriate suggestion regarding a meal for the user.

(13) According to the present embodiment, a program executed by a computer realizes an information acquisition function of acquiring user information on a user to whom food is to be provided, a recipe suggestion function of suggesting a plurality of recipes for dishes to the user based on the user information, a recipe selection result acquisition function of acquiring a result of a selection by the user from the plurality of recipes suggested by the recipe suggestion function, and a providing means selection result acquisition function of acquiring a result of a selection by the user for a dish providing means for the dish provided based on the recipe. This makes it possible to make a more appropriate suggestion regarding a meal for the user.

Note that the present invention is not limited to the above-described embodiments and modification, and various modifications and variations are possible. For example, the functions of the terminal device 10 and the system management server 20 may be provided in one information processing device, and the single device may be configured to infer a base recipe and dish providing means.

Alternatively, in the above-described embodiments, some or all of the functions of the terminal device 10, the system management server 20, and the like may be provided in a virtual server that is generated on another device or a cloud that can communicate via a network, and the functions of the food providing system 1 may be realized as a whole of the plurality of devices.

All or part of the functions of the food providing system 1 of the embodiments described above can be realized by hardware, software, or a combination thereof. Here, being realized by software means that the processor reads and executes a program to realize the functions. When configuring by hardware, part or all of the functions of the food providing system 1 may be configured with an integrated circuit (IC), such as an application specific integrated circuit (ASIC), a gate array, a field programmable gate array (FPGA), or a complex programmable logic device (CPLD).

When all or part of the functions of the food providing system 1 is configured by software, in a computer including a storage unit such as a hard disk or a ROM that stores a program describing all or part of the operation of the food providing system 1, a DRAM that stores data required for calculation, a CPU, and a bus that connects respective units, the DRAM stores information required for calculation and the CPU operates the program to realize the functions.

These programs can be stored using various types of computer readable media, and supplied to a computer. The computer readable media include various types of tangible storage media. Examples of the computer readable media include magnetic recording media (e.g., flexible disks, magnetic tapes, and hard disk drives), magnetic optical recording media (e.g., magnetic optical disks), CD-ROMs (read only memories), CD-Rs, CD-R/Ws, DVD-ROMs (digital versatile disks), DVD-Rs, DVD-R/Ws, semiconductor memories (e.g., mask ROMs, PROMs (programmable ROMs), EPROMs (erasable PROMs), flash memories, and RAMs (random access memories)). Alternatively, these programs may also be distributed by being downloaded to a user's computer over a network.

While embodiments of the present invention have been described in detail above, the foregoing embodiments have only shown specific examples in practicing the present invention. The technical scope of the present invention is not limited to the above-described embodiments. The present invention can be variously modified without departing from the spirit thereof, and they are also included in the technical scope of the present invention.

EXPLANATION OF REFERENCE NUMERALS

1 food providing system
10 terminal device
11, 21 processing unit
11*a* information input unit
11*b* base recipe display unit
11*c* base recipe selection reception unit
11*d* dish providing means display unit
11*e* dish providing means selection reception unit
12, 22, 32 ROM
13, 23, 33 RAM
14, 24, 34 input unit
15, 25, 35 display unit
16, 26, 36 storage unit
17, 27, 37 communication unit
20 system management server
21*a* information acquisition unit
21*b* health risk calculation unit
21*c* functional ingredient selection unit
21*d* base recipe suggestion unit
21*e* base recipe selection result acquisition unit
21*f* dish providing means estimation unit 21g dish providing means selection result acquisition unit
21h estimated information generation unit
21i delivery instruction unit
22 storage unit
22a user information database
22b health risk database
22c functional ingredient database
22d base recipe database
22e estimated information database
100, 200 machine learning unit
101, 201 state observation unit
102, 202 label acquisition unit
103, 203 learning unit
104, 204 output utilization unit
30 dish/ingredient delivery device
40 food production management device
50 ingredient database
60 restaurant terminal

The invention claimed is:

1. A food providing system, comprising:
a system management server communicatively connected to a terminal device of a user and a dish/ingredient delivery device, and a food production management device that cooks a dish based on a recipe ordered by the user, the system management server comprising:
a memory having a program stored thereon; and
a processor configured to execute the program stored on the memory to cause the system management server to:
acquire, from the terminal, user information on the user to whom food is to be provided;
estimate a selection probability of each type of providing of the dish of the dishes based on the user information;
output a plurality of recipes for dishes to the terminal device based on the user information in descending order of the selection probability;
acquire information on the recipe from an ingredient database that is a result of a selection by the user from the plurality of recipes suggested;
output, to the terminal device, each type of providing in descending order of the selection probability;
acquire a result of a selection, from the terminal device, by the user for a type of providing for a food provided based on the recipe;
transmit a delivery instruction to the dish/ingredient delivery device, wherein the delivery instruction includes the recipe selected by the user and the selected type of providing associated with the recipe selected by the user;
instruct, via the dish/ingredient delivery device and based on the delivery instruction, the food production management device to produce the food corresponding to the recipe selected by the user, wherein the food comprises the dish, one or more ingredients, or both; and
instruct the dish/ingredient delivery device to deliver the food produced by the food production management device to a home or a restaurant based on the selected type of providing selected by the user and the delivery instruction, wherein the selected type of providing indicates delivery of the one or more ingredients of the recipe to the home, delivery of the dish that has been cooked based on the recipe to the home, or serving of the dish based on the recipe at the restaurant.

2. The food providing system according to claim 1, wherein the processor is further configured to execute the program to further cause the system management server to select a functional ingredient effective for a health risk based on the user information.

3. The food providing system according to claim 1, wherein the suggesting the plurality of recipes comprises:
acquiring data relating to at least one of age/sex/medical history/allergy information of the user, a schedule for the user, fatigue of the user, gene information of the user, biological information and lifestyle information of the user, weather/temperature/atmospheric pressure, a social event, and a history of recent recipe selections, as input data;
acquiring a recipe selected in a past as a label; and
constructing a learning model for suggesting a recipe by performing supervised learning using a pair of the input data acquired and the label acquired as teaching data.

4. The food providing system according to claim 2, wherein the processor is further configured to execute the program to further cause the system management server to calculate a risk index for the health risk of the user based on the user information,
wherein the selecting the functional ingredient effective for the health risk is based on the risk index.

5. The food providing system according to claim 1, wherein the processor is further configured to execute the program to further cause the system management server to present an estimated price and an estimated required time for the selected type of providing.

6. The food providing system according to claim 1, wherein the estimating the selection probability comprises:
acquiring data relating to at least one of a schedule for the user, schedule for a family member of the user, schedule for a cook, a social event, family composition, fatigue of the user, weather/temperature/atmospheric pressure, a history of recent types of providing selections, and a household status, as input data;
acquiring the selected type of providing as a label; and
constructing a learning model for estimating a selection probability of each type of providing from a plurality of types of providing suggested to the user by performing supervised learning using a pair of the acquired data and the acquired label as teaching data.

7. The food providing system according to claim 1, wherein the processor is further configured to execute the program to further cause the system management server to instruct delivery of a functional ingredient effective for a health risk to a home or a facility for producing the dish based on the selected type of providing selected by the user.

8. The food providing system according to claim 7,
wherein the food production management device cooks the dish corresponding to the recipe and with the functional ingredient added.

9. The food providing system according to claim 8, wherein the processor is further configured to execute the program to further cause the dish/ingredient delivery device to group orders whose scheduled eating time is within a predetermined period of time, classify orders corresponding to a same recipe among orders in a same group as a subgroup, and adjust a plurality of schedules for ordered cooking based on the classification.

10. The food providing system according to claim 8, wherein the processor is further configured to execute the program to further cause dish/ingredient delivery device to plan personnel or a vehicle to be allocated to delivery based on a selection probability of each of the types of providing estimated based on the user information.

11. A food providing method executed by a system management server communicatively connected to a terminal device of a user and a dish/ingredient delivery device that provides a food to the user, the method comprising:

acquiring, by the system management server, from the terminal user information on the user to whom food is to be provided;

estimating a selection probability of each type of providing of the dish of the dishes based on the user information;

outputting, by the system management server, to a terminal device of the user a plurality of recipes for dishes based on the user information in descending order of the selection probability;

acquiring, by the system management server, from an ingredient database information on a recipe that is a result of a selection by the user from the plurality of recipes suggested;

outputting, by the system management server, to the terminal device of the user each type of providing in descending order of the selection probability;

acquiring, by the system management server, from the terminal device of the user a result of a selection by the user for a type of providing for a food provided based on the recipe;

transmitting a delivery instruction to the dish/ingredient delivery device, wherein the delivery instruction includes the recipe selected by the user and the selected type of providing associated with the recipe selected by the user;

instructing, via the dish/ingredient delivery device and based on the delivery instruction, the food production management device to produce the food corresponding to the recipe selected by the user, wherein the food comprises the dish, one or more ingredients, or both; and instructing the dish/ingredient delivery device to deliver the food produced by the food production management device to a home or a restaurant based on the selected type of providing selected by the user and the delivery instruction, wherein the selected type of providing indicates delivery of the one or more ingredients of the recipe to the home, delivery of the dish that has been cooked based on the recipe to the home, or serving of the dish based on the recipe at the restaurant.

12. A non-transitory computer-readable media of a computer having a program stored thereon, the program when executed by a processor of the computer causing the computer to:

communicatively connect to a terminal device of a user, a dish/ingredient delivery device, and a food production management device that cooks a dish based on a recipe ordered by the user;

acquire, from the terminal device, user information on the user to whom food is to be provided;

estimate a selection probability of each type of providing of the dish of the dishes based on the user information;

output a plurality of recipes for dishes to the terminal device based on the user information in descending order of the selection probability;

acquire information on the recipe from an ingredient database that is a result of a selection by the user from the plurality of recipes suggested;

output, to the terminal device, each type of providing in descending order of the selection probability;

acquire a result of a selection by the user, from the terminal device, for a type of providing for a food provided based on the recipe;

transmit a delivery instruction to the dish/ingredient delivery device, wherein the delivery instruction includes the recipe selected by the user and the selected type of providing associated with the recipe selected by the user;

instruct, via the dish/ingredient delivery device and based on the delivery instruction, the food production management device to produce the food corresponding to the recipe selected by the user, wherein the food comprises the dish, one or more ingredients, or both; and instruct the dish/ingredient delivery device to deliver the food produced by the food production management device to a home or a restaurant based on the selected type of providing selected by the user and the delivery instruction, wherein the selected type of providing indicates delivery of the one or more ingredients of the recipe to the home, delivery of the dish that has been cooked based on the recipe to the home, or serving of the dish based on the recipe at the restaurant.

* * * * *